Figure 3A:
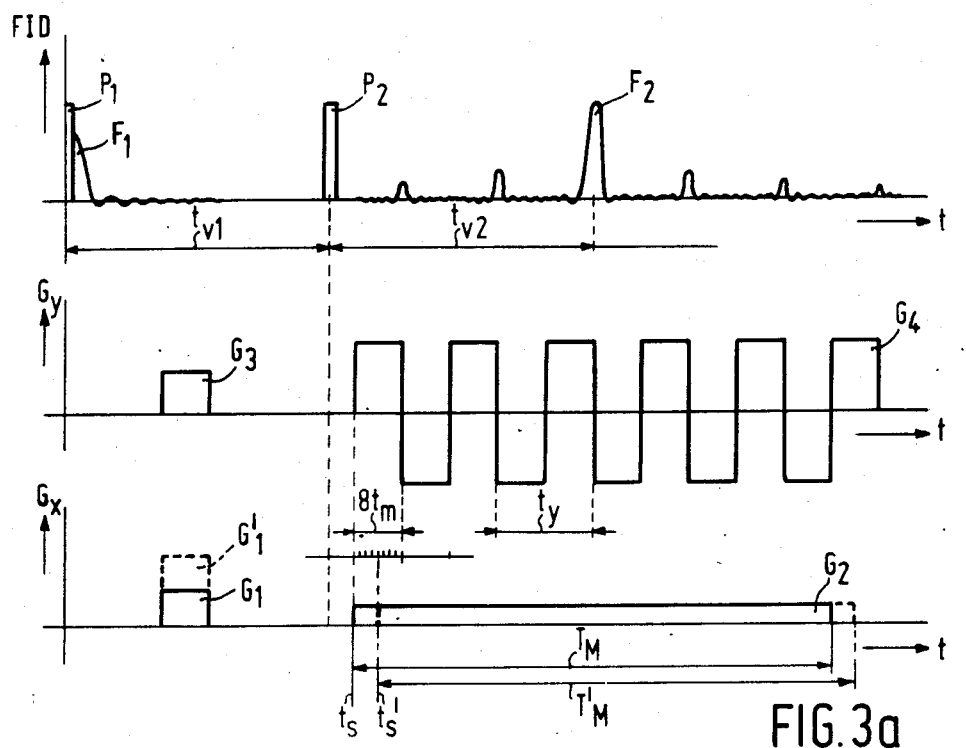

United States Patent [19]

Cuppen et al.

[11] Patent Number: 4,707,660
[45] Date of Patent: Nov. 17, 1987

[54] FAST METHOD AND DEVICE FOR DETERMINING AN NMR DISTRIBUTION IN A REGION OF A BODY

[75] Inventors: Johannes J. M. Cuppen; Johannes P. Groen, both of Eindhoven, Netherlands

[73] Assignee: U.S. Philips Corporation, New York, N.Y.

[21] Appl. No.: 768,400

[22] Filed: Aug. 22, 1985

[30] Foreign Application Priority Data

Sep. 10, 1984 [NL] Netherlands .......................... 8402752
Nov. 28, 1984 [NL] Netherlands .......................... 8403611

[51] Int. Cl.$^4$ ............................................. G01R 33/20
[52] U.S. Cl. ...................................... 324/309; 324/307
[58] Field of Search ............... 324/300, 307, 309, 313, 324/314, 318, 322

[56] References Cited

U.S. PATENT DOCUMENTS

| | | | |
|---|---|---|---|
| 4,384,255 | 5/1983 | Young et al. ........................ | 324/312 |
| 4,509,015 | 4/1985 | Ordidge ............................... | 324/309 |
| 4,527,124 | 7/1985 | Uijen ................................... | 324/307 |

Primary Examiner—Michael J. Tokar
Attorney, Agent, or Firm—Robert T. Mayer; Algy Tamoshunas

[57] ABSTRACT

The invention relates to the determination of an NMR distribution in which an alternating gradient field is applied while sampling the NMR signal (FID signal, nuclear spin echo signal). The frequency of the alternating gradient field is comparatively low (order of magnitude of 100 Hz) and the field has from a few to some tens of cycles during each measurement period. While an FID signal is being sampled, the image frequency field matrix is scanned using a zig-zag (oscillating) line pattern during each line when data is provided for elements in from a few to some tens of rows in the image frequency matrix. By applying preparation gradient fields, the image frequency matrix can be filled by means of successive zig-zag line patterns which have been shifted with respect to one another and which thus enable a uniform sampling density to be provided in the image frequency space. The filling of the image frequency matrix with signal samples is thus speeded up by a factor of a few to some tens of times by the invention, the energy required for controlling the gradient field coils being substantially reduced at the same time.

27 Claims, 14 Drawing Figures

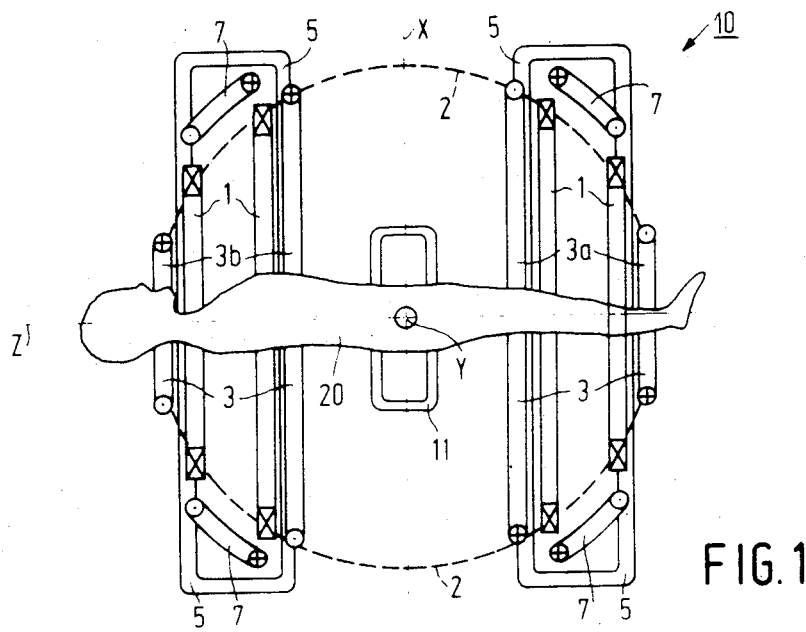
FIG. 1
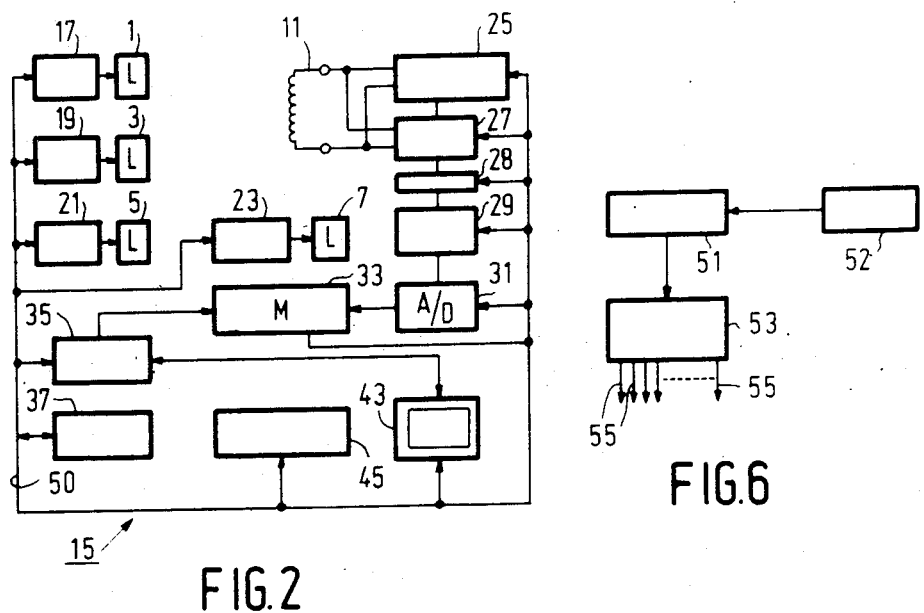
FIG. 2
FIG. 6

FAST METHOD AND DEVICE FOR DETERMINING AN NMR DISTRIBUTION IN A REGION OF A BODY

The invention relates to a method of determining an NMR distribution in a region of a body which is situated in a steady, uniform magnetic field, including the steps of:
 (a) generating an r.f. electromagnetic pulse in order to cause a precessional motion of the magnetization of the nuclei in the body, thus generating a resonance signal,
 (b) then generating, after a preparation period, an alternating, periodic gradient magnetic field during a measurement period or several measurement periods, said measurement period (periods) being divided into a plurality of sampling intervals for taking a corresponding number of signal samples of the resonance signal,
 (c) then repeating, each time after a waiting period, the steps (a) and (b) a plurality of times, the duration of the preparation period and/or the integral over the preparation period of at least one gradient magnetic field applied during the preparation period each time having a different value in order to provide a set of signal samples from which, after a signal transformation thereof, an image of a nuclear magnetization distribution is determined.

The invention also relates to a device for determining an NMR distribution in a region of a body, comprising:
 (a) means for generating a steady, uniform magnetic field,
 (b) means for generating r.f. electromagnetic radiation,
 (c) means for generating a gradient magnetic field,
 (d) means for generating an alternating, periodic gradient magnetic field,
 (e) sampling means for taking signal samples of a resonance signal generated by the means specified in paragraphs (a) and (b) in the presence of an alternating gradient magnetic field generated by the means specified in paragraph (d),
 (f) processing means for processing the signal samples in order to obtain an NMR distribution, and
 (g) control means for controlling at least the means specified in paragraphs (b) to (f) for generating, conditioning, and sampling a plurality of resonance signals and for processing the signal samples.

Such a method and device are known from Netherlands Patent Application corresponding to U.S. Pat. No. 4,527,124. During the measurement period in the known method a periodic, alternating gradient magnetic field is generated whose period equals the sampling interval, at least one additional signal sample being taken in each sampling interval.

As explained in said Netherlands Patent Application No. NL-A-82.03519, the use of the alternating gradient magnetic field and the taking of additional signal samples ensure that at least two rows of a (two-dimensional) image frequency matrix will have been filled after the sampling of a resonance signal (FID or spin echo signal). Thus, the duration of a measurement cycle is reduced to one half (one third, one quarter) when one (two, three) additional signal samples are taken, respectively. Because the duration of a resonance signal amounts to only some tens of milliseconds, the taking of 128 or 256 signal samples (in a row in the image frequency matrix) will require a sampling interval of the order of magnitude of 100 μs, which means that the frequency of the additional gradient magnetic field must amount to 10 kHz. This comparatively high frequency for the alternating gradient magnetic field limits the maximum number of rows of the image frequency matrix which can be filled by sampling a single resonance signal. The maximum distance Δk between two rows filled by sampling a resonance signal amounts to $$\Delta k = \int_0^{\frac{1}{2}t_m} \gamma \cdot G(\tau) \cdot d\tau,$$

in which $\frac{1}{2}t_m$ is the first half period of the periodic alternating gradient magnetic field, $\gamma$ is the gyromagnetic ratio and $g(\tau)$ is the alternating gradient magnetic field. The maximum distance Δk determines the maximum number of rows in the image frequency matrix filled after sampling a resonance signal and is proportional to the amplitude of the applied alternating gradient magnetic field. The amplitude of the alternating gradient magnetic field cannot be increased at will, because the rate of change (dG/dt) of the alternating gradient magnetic field must remain within imposed health safety limits. This rate of change (dG/dt) is proportional to the product of the amplitude and the frequency of the additional gradient magnetic field. Because the frequency itself is already comparatively high (10 kHz), a maximum permissible amplitude will be quickly reached.

It is also to be noted that the energy required for operating the gradient coils increases with the frequency of the magnetic field; when the energy to be applied to the gradient coils is increased, the eddy currents in the metal parts of the magnet for generating the main field also increase, which is undesirable. The first effect means that comparatively expensive (amplifier) equipment will be required, which is also a drawback.

It is an object of the invention to provide a method and a device in which it is not necessary to generate an alternating, periodic gradient magnetic field having a comparatively high frequency, and in which the time period required for making an image having a resolution which at least equals that obtained with the prior art method and device is the same or shorter.

It is a further object of the invention to provide a method and a device such that defects in an image of the nuclear magnetization distribution which are caused by non-uniformities of the uniform magnetic field, local susceptibility transitions and "chemical shift" ($\sigma$) of the resonance frequency of bound nuclei are eliminated or substantially reduced.

To achieve this, a method in accordance with the invention is characterized in that the period of the sampling interval is at least a factor 2 shorter than the period of the alternating periodic gradient magnetic field which at the most equals the measurement period. The method in accordance with the invention utilizes an alternating periodic gradient magnetic field having a comparatively low frequency (having an order of magnitude of 100 Hz) so that the amplitude may be greater. Because the period of duration is also longer, the integral $$\int_0^{\frac{1}{2}t_m} \gamma \cdot G(\tau) \cdot d\tau$$

can reach such a high value that the maximum image frequency (for example, $k_{ymax}$) is reached in the image frequency matrix. When a second (constant) gradient field ($G_x$) is present during the alternating, periodic gradient field, the signal samples to be taken will be situated on a curve which oscillates (at a low frequency) between the image frequencies 0 and $k_{ymax}$ (or between $-k_{ymax}$ and $+k_{ymax}$) (for example from 4 to 16 times), the image frequency $k_x$ then increasing from a minimum value (for example, $-k_{xmax}$) to a maximum value (for example, $+k_{xmax}$). In this way a number of (oblique or even curved) rows (from 4 to 16) in the image frequency matrix are thus filled.

A preferred version of a method in accordance with the invention in which a steady, uniform magnetic field is generated in the region where the body is situated and which includes the steps of:

(a) generating during a preparation period, an r.f. electromagnetic pulse in order to cause a precessional motion of the magnetization of the nuclei in the body, thus generating a resonance signal, (b) then after the preparation period, generating an alternating, periodic gradient magnetic field during a measurement period or several measurement periods, said measurement period (periods) being divided into a plurality of sampling intervals for taking a corresponding number of signal samples of the resonance signal, (c) then repeating, each time after a waiting period, the steps (a) and (b) a plurality of times, the duration of the preparation period having a different value during each repetition in order to provide a set of signal samples from which, after a signal transformation thereof, an image of a nuclear magnetization distribution is determined, is characterized in that the period of the sampling interval is at least a factor 2 shorter than the period of the alternating periodic gradient magnetic field which at most equals the measurement period, the starting instant of the alternating, periodic gradient magnetic field being coincident with the end of the preparation period, the measurement period (periods) commencing each time at the same time interval after the r.f. electromagnetic pulse (pulses), so that at the (successive) starting instant (instants) of the measurement period (periods) the phase of the alternating, periodic gradient magnetic field is always made different by using each time a different preparation period.

The preferred version of the method in accordance with the invention offers the advantage that all signal samples associated with the image frequencies $k_x$ are taken at the same instant after the generation of the r.f. electromagnetic pulse (excitation pulse or 180° echo pulse). This means that these signal samples have all been subject to the same effect with respect to, for example, spin-spin relaxation ($T_2$-period), field non-uniformity etc., the effect, moreover, being directly dependent on the value of the image frequency $k_x$. This results in an image which contains less artefacts such as ghost images and blurring due to $T_2$-time effects and field non-uniformities in the steady main magnetic field Bo.

As known, the precessional frequency of the nuclear magnetization M is often defined by the formula $\omega = \gamma \cdot B$, in which $\gamma$ is the gyromagnetic ratio and B is the intensity of the magnetic field. The gyromagnetic ratio $\gamma$ depends on the type of nucleus only if the nucleus is considered to be free. Usually nuclei are not considered to be free, because they are affected by binding electrons about the nucleus. This becomes apparent as the so-called chemical shift: the bound nucleus does not resonate at $\omega = \gamma \cdot B$, but rather at $\omega' = \gamma \cdot B \cdot (1-\sigma)$. Both the angular frequency $\omega'$ and the shift $\Delta\omega = \omega - \omega' = \gamma \cdot B \cdot \sigma$ are proportional to the magnetic field B. The value of $\sigma$ is generally very small (having an order of magnitude of $10^{-6}$). If the intensity of the magnetic field B is sufficiently high (for example, 1.5 T) this chemical shift $\sigma$ can cause defects in an image of the proton density in a body. The shift $\Delta\omega$ for protons in water with respect to protons in fat amounts to 200 Hz for a field strength of 1.5 T ($\sigma \approx 3.5 \cdot 10^{-6}$). The appearance of image defects due to the chemical shift $\sigma$ will now be described. An image of a body is composed of a matrix of pixels. When a row of pixels is considered which extends in the gradient direction of a gradient magnetic field, a bandwidth $\Delta\omega_y = \gamma G_y \cdot \Delta_y$ can be determined from the width (for example, $\Delta y$) of such a pixel and the intensity of the gradient magnetic field, $G_y$ being the gradient intensity of the gradient field. When the bandwidth $\Delta\omega_y$ for a pixel is smaller than the shift $\Delta\omega$ due to the chemical shift for fat in a given region of the body, the proton density of the fat will be imaged in a pixel other than the proton density of the water in the same region of the body, thus causing said image defects. The foregoing can be avoided by increasing the intensity of the gradient field which, however, results in an undesirable lower signal-to-noise ratio.

Non-uniformities of the steady field may also cause image defects which are really distortions of the image of the actual situations. Furthermore, susceptibility differences also cause deformations of the "actual" image. Such differences may locally reach very high values (up to 9 ppm, compare $\sigma \approx 3.5$ ppm). When an applied gradient magnetic field is not (much) stronger than a local gradient due to non-uniformity and susceptibility differences, pronounced image distortion will occur which causes one part of the image to be shifted over another part. The local intensities are also affected because in the distorted (shifted) part the image intensity is retained (and actually superposed on the intensity of another part of the image). This causes intensity increases and decreases at contours of organs in medical images which could be incorrectly interpreted (layers of fat concentrations where there are no concentrations?). The effect of such non-uniformities and susceptibility differences can be (partly) eliminated by choosing a very strong gradient magnetic field. However, a drawback of this solution is that the bandwidth of the nuclear spin resonance signal to be received becomes very wide, which results in a poor signal-to-noise ratio.

In order to obtain an image of an NMR distribution without the defects caused by chemical shift, non-uniformities of the steady (main) magnetic field and local susceptibility differences, a version of the method in accordance with the invention is characterized in that during the measurement period only the alternating gradient magnetic field is applied so that, after the signal transformation has been applied to the signal samples, there is obtained for each pixel a frequency spectrum in which the intensities of the nuclear spins, whether bound or not, can be distinguished, after which an image of a magnetization distribution of a given type of nuclear spin is formed by selecting, for each pixel, the intensity of a selected type of nuclear spin from the frequency spectrum associated with the relevant pixel.

An image of an NMR distribution thus obtained is (substantially) free of the described defects, which can be understood as follows. The chemical shift causes intensity peaks in the frequency spectrum which are always situated at the same distance from one another so that they can be recognized. Magnetic field non-uniformities and local susceptibility differences cause a local field strength variation and hence a frequency shift of said intensity peaks in the frequency spectrum. When a sufficiently wide frequency spectrum is measured for each pixel and the recognizable intensity peaks are selected from this spectrum, the frequency shifts are cancelled. For example, for the determination of a proton density distribution it is now possible to form a distortion-free image of a distribution of "free protons" (water), "bound protons" (fat) and the total protons (water + fat) by adding in the latter case the intensity peaks of "water" and of "fat" from the frequency spectrum for each pixel.

A device in accordance with the invention is characterized in that the control means comprise programmed computer means for generating and applying control signals to the means for generating the alternating gradient magnetic field, said generated gradient magnetic field having a period which is at least a factor 2 longer than the period of a sampling interval and which at the most equals the measurement period during which the resonance signal is sampled.

A preferred embodiment of a device in accordance with the invention is characterized in that the programmed computer means adjusts different preparation periods during successive measurement cycles, supplies a start pulse for the alternating gradient magnetic field so that the beginning thereof coincides with the end of the preparation period, and supplies a start pulse for the process of sampling the resonance signal, each time with the same time delay after the beginning of the preparation period.

A further embodiment of a device in accordance with the invention which produces images of nuclear magnetization distributions which do not include defects caused by chemical shifts, non-uniformities in the steady magnetic field or local susceptibility differences is characterized in that the processing means includes storage means for the storage of a frequency spectrum to be formed from the signal samples for each pixel of the image of the nuclear magnetization distribution to be determined and also includes selection means for selecting an intensity value for the associated pixel from each frequency spectrum.

Figure 3B:
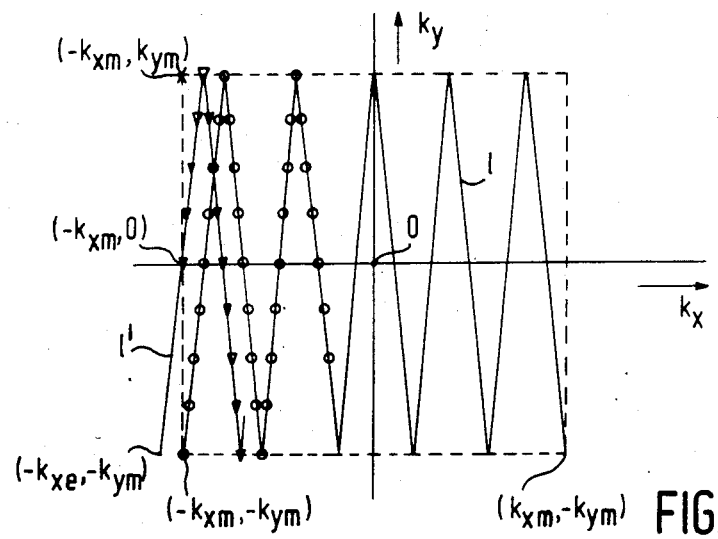
Figure 4A:
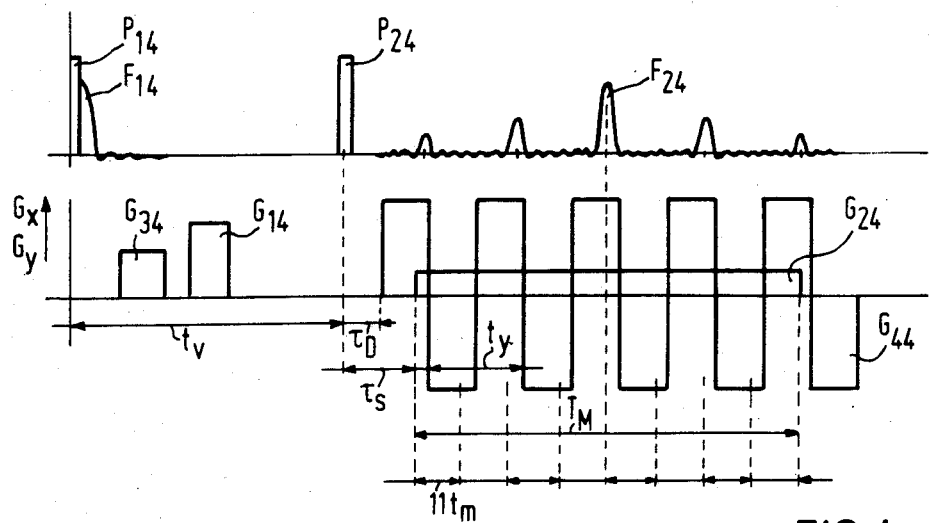
Figure 4B:
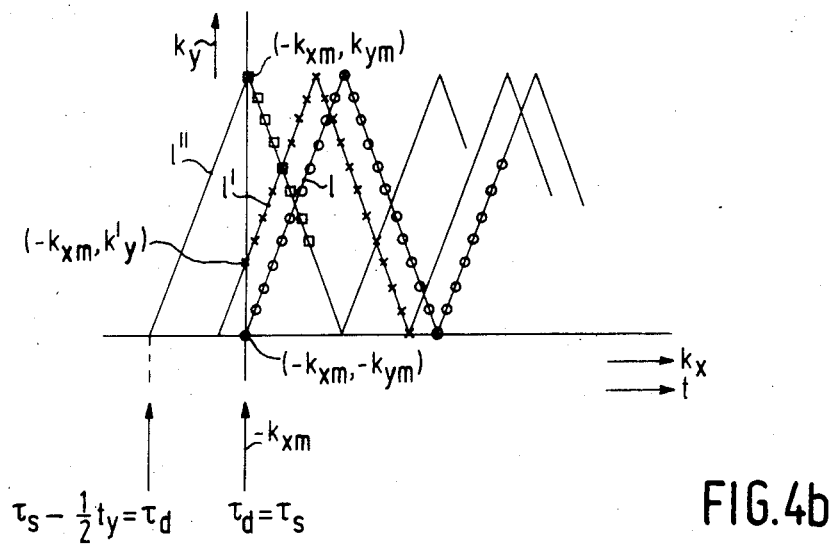
Figure 5A:
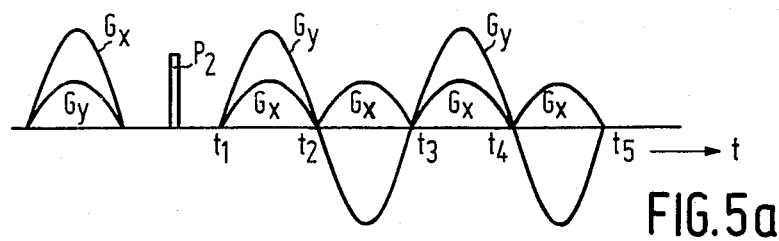
Figure 7:
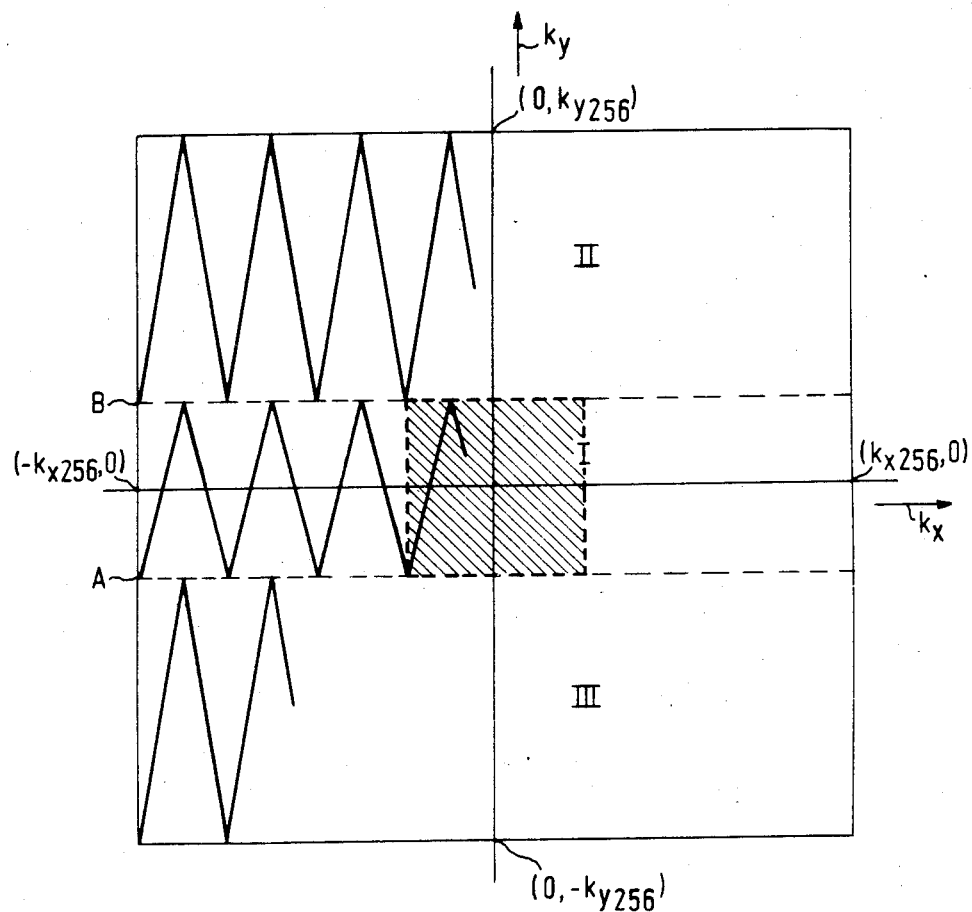
Figure 8:
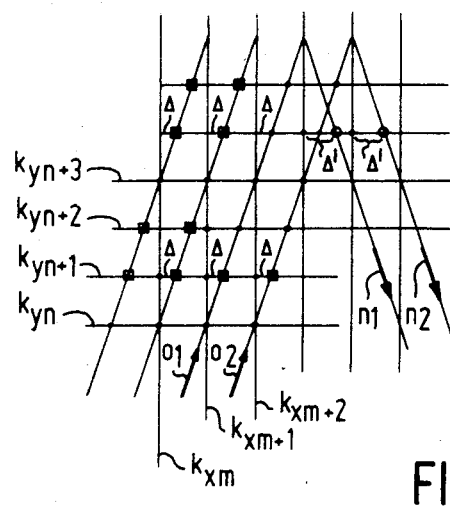
Figure 9A:
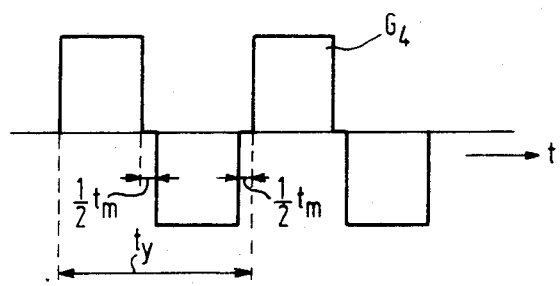

Embodiments in accordance with the invention will be described in detail hereinafter with reference to the drawing; therein:

FIG. 1 shows diagrammatically a configuration of a coil system of a device for performing a method in accordance with the invention, FIG. 2 shows a block diagram of a device for performing the method in accordance with the invention, FIGS. 3a and 3b are diagrams illustrating a simple version of a method in accordance with the invention, FIGS. 4a and 4b are diagrams illustrating preferred versions of a method in accordance with the invention, FIGS. 5a, b and c are time diagrams illustrating further versions of a method in accordance with the invention, FIG. 6 illustrates a part of a device for performing the method in accordance with the invention, FIG. 7 is a diagram showing a further version of a method in accordance with the invention, FIG. 8 is a diagram illustrating the shifting of measurement points in the image frequency plane, and FIGS. 9a and b are diagrams showing a version of an alternating gradient field and associated measurement points in the image frequency matrix.

FIG. 1 shows a coil system 10 which forms part of a device 15 (FIG. 2) used for determining an NMR distribution in a region of a body 20. This region has a thickness of, for example $\Delta z$ and is situated in the x-y plane of the x-y-z coordinate system shown. The y-axis of the system extends upwardly perpendicular to the plane of drawing. The coil system 10 generates a uniform, steady magnetic field Bo having a field direction parallel to the z-axis, three gradient magnetic fields $G_x$, $G_y$, $G_z$ having a field direction parallel to the z-axis and a gradient direction parallel to the x, y and z-axis, respectively, and an r.f. magnetic field. To achieve this, the coil system 10 comprises a set of main coils 1 for generating the steady uniform magnetic field Bo. The main coils may be arranged, for example on the surface of a sphere 2 whose centre is situated at the origin O of the cartesian coordinate system x, y, z shown, the axes of the main coils 1 being coincident with the z-axis.

The coil system 10 furthermore comprises four coils 3a, 3b for generating the gradient magnetic field $G_z$. To achieve this, a first set 3a is excited by a current in the opposite sense with respect to the current direction in the second set 3b; this is denoted by (·) and (x) in the Figure. Therein (·) means a current entering the section of the coil 3 and (x) means a current leaving the section of the coil.

The coil system 10 also comprises four rectangular coils 5 (only two of which are shown) or four other coils such as, for example "Golay-coils", for generating the gradient magnetic field $G_y$. In order to generate the gradient magnetic field $G_x$, use is made of four coils 7 which have the same shape as the coils 5 and which have been rotated through an angle of 90° about the z-axis with respect to the coils 5. FIG. 1 also shows a coil 11 for generating and detecting an r.f. electromagnetic field.

FIG. 2 shows a device 15 for performing a method in accordance with the invention. The device 15 comprises coils 1, 3, 5, 7 and 11 which have already been described with reference to FIG. 1, current generators 17, 19, 21 and 23 for the excitation of the coils 1, 3, 5 and 7, respectively, and an r.f. signal generator 25 for the excitation of the coil 11. The device 15 also comprises a high-frequency signal detector 27, a demodulator 28, a sampling circuit 29, processing means such as an analog-to-digital converter 31, a memory 33 and an arithmetic circuit 35 for performing a Fourier transformation, a control unit 37 for controlling the sampling instants, and also a display device 43 and central control means 45 whose functions and relationships will be described in detail hereinafter.

The device 15 performs a method of determining the NMR distribution in a region of the body 20 as will be described hereinafter. The method involves the frequent repetition of a measurement cycle which itself can be divided into several steps. During a measurement cycle, some of the nuclear spins present in the body are resonantly excited. For resonant excitation of the nuclear spins, the current generator 17 is switched on by the central control unit 45 so that the coil 1 is energized and remains energized for a desired number of measurement cycles. A steady and uniform magnetic field Bo is thus generated. Furthermore, the r.f. generator 25 is switched on for a short period of time, so that the coil 11 generates an r.f. electromagnetic field. The nuclear spins in the body 20 can be excited by the applied magnetic fields, the excited nuclear magnetization then enclosing a given angle, for example 90° (90° r.f. pulse) with respect to the direction of the uniform magnetic field Bo. The position and the kind of spin nuclii which will be excited will depend inter alia on the intensity of the field Bo, on the gradient magnetic field or fields that are applied and on the angular frequency $\omega$ of the r.f. electromagnetic field, because the equation $\omega = \gamma \cdot Bo$ (1) must be satisfied, in which $\gamma$ is the gyromagnetic ratio (for free protons, for example $H_2O$ protons, $\gamma/2\cdot\pi = 42.576$ MHz/T). After an excitation period, the r.f. generator 25 is switched off by the central control means 45. The resonant excitation is always performed at the beginning of each measurement cycle. For some methods of operation, r.f. pulses are also generated during the measurement cycle. These r.f. pulses are then, for example, a series of 180° r.f. pulses which are periodically generated. The latter is referred to as "spin echo". Spin echo is inter alia described in the article by I. L. Pykett "NMR in Medicine" published in Scientific American, May 1982.

Signal samples are collected during the next step. For this purpose use can be made of the gradient fields which are generated by the generators 19, 21, 23, respectively under the control of the central control means 45. The detection of the resonance signal (referred to as an FID signal) is performed by switching on the r.f. detector 27, the demodulator 28, the sampling circuit 29, the analog-to-digital converter 31, and the control unit 37. This FID signal appears as a result of the precessional motion of the nuclear magnetizations about the field direction of the magnetic field Bo due to the r.f. excitation pulse. This nuclear magnetization induces an induction voltage in the detection coil whose amplitude is a measure of the nuclear magnetization.

The analog, sampled FID signals supplied by the sampling circuit 29 are digitized by converters 31 and stored in a memory 33. After a final signal sample has been taken during a measurement cycle, the central control means 45 deactivates the generators 19, 21 and 23, the sampling circuit 21, the control unit 37 and the analog-to-digital converter 31.

The sampled FID signal is and remains stored in the memory 33. Subsequently, a next measurement cycle is performed during which an FID signal is again generated, sampled and stored in the memory 33. When a sufficient number of FID signals have been measured (the number of FID signals to be measured depends, for example on the desired resolution), a 2-D or 3-D image of a nuclear magnetization distribution can be determined via a signal transformation (for example, a 2-D or 3-D Fourier transformation, depending on the use of the gradient magnetic fields under whose effect the FID signals are generated and sampled).

FIG. 3a shows an example of a measurement cycle in accordance with the invention which will be described with reference to the device 15 shown in FIG. 2. After switching on the main coils 1 which generate a steady, uniform magnetic field Bo, a 90° pulse $P_1$ is generated by means of the r.f. coil 11. Resultant resonance signal $F_1$ is allowed to decay when using the spin echo technique, and after a period $t_{v1}$, a 180° pulse $P_2$ is generated by the r.f. coil 11. During a part of the period $t_{v1}$, gradient fields $G_x$ and $G_y$ (denoted by curves $G_1$ and $G_3$) are generated for reasons to be described hereinafter. After a period of time $t_{v2}$ which is equal to $t_{v1}$, an echo resonance signal $F_2$ produced by the 180° pulse $P_2$ will reach a peak value. The use of the so-called spin echo technique (180° pulse $P_2$) prevents the occurrence of phase errors in the resonance signals produced by nuclear spins; such phase errors are caused by non-uniformities in the steady magnetic field Bo. The echo resonance signal is sampled each time after a sampling interval $t_m$ in the presence of a constant gradient field $G_x$ which is denoted by a curve $G_2$.

It is known that the phase angle of a magnetization at a point x in a gradient magnetic field $G_x$ is determined by $$\int^t \gamma \cdot G_x \cdot x \cdot d\tau$$

Thus, an image frequency $k_x$ can be defined as $$k_x = \gamma \cdot \int^t G_x \cdot d\tau$$

Thus, after each sampling period $t_m$ a corresponding signal sample is determined which is associated with a different image frequency $k_x$. The successive image frequencies exhibit an image frequency difference $$\Delta k_x = \gamma \cdot \int_{t_m} G_x \cdot d\tau$$

It will be apparent that when a gradient field $G_y$ is applied for some time, signal samples are obtained which are associated with image frequency pairs ($k_x$, $k_y$). In the absence of a gradient magnetic field $G_y$, signal samples are obtained which are associated with the image frequencies ($k_x$, 0). It can be demonstrated that when a group of signal samples are collected which are associated with a matrix of image frequency pairs $k_x$, $k_y$ in which the image frequencies range from $-k_{xm}$ to $+k_{xm}$ and from $-k_{ym}$ to $+k_{ym}$, a magnetization distribution in an x-y plane can be determined from this group of signal samples via a 2-D Fourier transformation, $|k_{xm}|$ and $|k_{ym}|$ then being the highest image frequencies occurring in the matrix. Thus, for determining an NMR distribution it is necessary to take signal samples which are associated with image frequencies betwen $-k_{xm}$ and $+k_{xm}$ and between $-k_{ym}$ and $+k_{ym}$. The image frequency $k_y$ is given by $$k_y = \gamma \cdot \int^t G_y(\tau)d\tau$$

Because a periodic, alternating gradient magnetic field $G_y$ is present during the measurement period $T_M$, the image frequency $k_y$ will oscillate during a minimum value and a maximum value. The amplitude $G_4$ and the period $t_y$ of the gradient field $G_y$ should be chosen so that the minimum value equals $-k_{ym}$ and the maximum value equals $+k_{ym}$. During the preparation period $t_{v1}$, the two gradient fields $G_x$ and $G_y$ are applied for a (short) period of time, for example in such a manner that during a first measurement cycle $$k_{xm} = \gamma \cdot \int_{t_m} G1 \cdot dt \text{ and } k_{ym} = \gamma \cdot \int_{t_m} G_3 \cdot dt.$$

As a result, the first signal sample which is taken during the measurement period $T_M$ following the preparation period $t_{v1}$ is associated with the image frequency pair $(-k_{xm}, k_{ym})$, because the 180° pulse reverses the effect of the gradient fields exerted thus far. During the measurement period, both the alternating $G_y$ gradient magnetic field $G_4$ and the constant $G_x$ gradient field $G_2$ are present. The $k_y$ image frequency will thus oscillate between $-k_{ym}$ and $+k_{ym}$, whilst the $k_x$ image frequency will increase for $-k_{xm}$ to $+k_{xm}$. As a result, all signal samples taken during the measurement period $T_M$ will be situated on the sawtooth line 1 which starts at the point $-k_{xm}, -k_{ym}$, extends through the entire image frequency matrix and terminates at the point $(k_{xm}, -k_{ym})$. For the sake of clarity, the half period $(\frac{1}{2}t_y)$ of the alternating $G_y$ gradient field $G_4$ is divided into only 8 sampling intervals (8 tm). In reality the half period $(\frac{1}{2}t_y)$ is divided into, for example 128, 256 or 512 sampling intervals. During a measurement period $T_M$ 10 "rows" of the image frequency matrix are thus filled with signal samples as denoted (partly) by O on the line 1 in FIG. 3b.

In order to fill the image frequency matrix $(k_x, k_y)$ with a regular pattern (which is desirable if an image of the NMR distribution is to be determined by means of a Fourier transformation), a stronger $G_x$ gradient field $G'_1$ is applied during the preparation period for a subsequent measurement period, the intensity and the duration of the $G_y$ gradient field $G_3$ remaining the same. If a signal sample were taken after the termination of the 180° echo pulse $P_2$ and before the activation of the $G_x$ gradient field $G_2$ and the alternating $G_y$ gradient field $G_4$, it would be associated with the image frequency pair $(-k_{xe}, -k_{ym})$ in which $$-k_{xe} = -\gamma \cdot \int_t G'_1 \cdot dt.$$

Consequently, after the application of the $G_x$ gradient field $G_2$ and the alternating $G_y$ gradient field $G_4$ a waiting period is introduced before a sampling instant $t'_s$, which is chosen so that the first sample at the instant $t'_s$ is associated with the image frequency $-k_{xm}$. Consequently, the following must hold good:

$$-k_{xe} + k_{xm} = \gamma \cdot \int_{t_s}^{t'_s} G_2 \cdot dt,$$

and similarly $$-k_{xe} + k_{xm} = -\gamma \cdot \int_t ((G'_1 - G_1) \cdot dt).$$

By choosing a different value for $-k_{xe}$ and hence for an associated first sampling instant $t'_s$ in the successive measurement cycles, each first signal sample will be determined for an image frequency pair $(-k_{xm}, k_{yi})$, in which $k_{yi}$ will have an associated value in the range $-k_{ym}$ to $+k_{ym}$. Consequently, the curve 1 will be shifted in the $k_x, k_y$ image frequency plane (FIG. 3b) to the position 1' shown in FIG. 3b, the signal samples then being situated at a regular distance from the signal samples taken during the preceding measurement cycle. It will be evident that the entire measurement period $T'_M$ will be shifted a period of time $t_x - t'_s$ with respect to the measurement period $T_M$ of the preceding measurement cycle. It will be apparent that, in reality, a number of measurement cycles will need to be completed before the measurement period shift $t'_s - t_s$ which is given here by way of example has taken place (in other words, several further sawtooths will preferably be inserted equidistantly between the sawtooths 1 and 1'). It will also be apparent that the maximum measurement period shift required, amounts to half the period $t_y$. When this measurement period shift $\frac{1}{2}t_y$ has taken place, a uniform spacing of signal samples will be provided throughout the image frequency matrix by repeating all the preceding measurement cycles, during which the amplitude of the $G_y$ gradient field $G_3$ during the preparation period as well as that of the $G_y$ gradient field $G_4$ is inverted. Consequently, the sawtooths 1 and 1' will then be arranged, in effect, "upside down" in the image frequency matrix, with the result that the desired uniform filling of the image frequency matrix with signal samples will be obtained. It is to be noted that, if no further steps are taken, a signal sample will be taken twice for each image frequency pair $(k_x, k_y)$; however, this will contribute to an improved signal-to-noise ratio.

Various alternatives exist for the described sampling diagram (filling diagram for the $k_x - k_y$ matrix). One possibility would be to generate a 180° pulse after deactivating the $G_x$ and $G_y$ gradient magnetic field after the expiration of the measurement period $T_M$ or $(T'_M)$, said 180° pulse inverting the state of the nuclear spins so that when the $G_x$ gradient field and the inverted $G_y$ gradient field are activated again, a sawtooth line would be followed in FIG. 3b corresponding to that generated by rotating the sawtooth line 1 (or 1') 180° about the $k_x$-axis. The foregoing will hold good only if the alternating $G_y$ gradient field is applied for an integral number of periods.

FIGS. 4a and 4b show the principle of a preferred version of a method in accordance with the invention. Using a 90° excitation pulse $P_{14}$, a resonance signal $F_{14}$ is generated which decays in the course of time. Using a 180° echo pulse $P_{24}$, an echo resonance signal $F_{24}$ is generated and sampled. During the period $t_v$ between the 90° and the 180° pulses $P_{14}$ and $P_{24}$, $G_x$ and $G_y$ preparation gradient fields $G_{14}$ and $G_{34}$, respectively, are apppplied, for which $$k_{xm} = \gamma \cdot \int_{t_v} G_{14} \cdot dt \text{ and } k_{ym} = \gamma \cdot \int_{t_v} G_{34} \cdot dt,$$

so that the image frequency matrix can always be filled starting from the same side $(-k_{xm})$ for reasons to be explained hereinafter. The measurement period $T_M$ always commences the same period of time $t_s$ after the 180° pulse, (or $t_v + \tau_s$ after the 90° pulse), a constant $G_x$ gradient field $G_{24}$ then being applied. The periodic, alternating $G_y$ gradient field $G_{44}$ is switched on a period of time $\tau_d$ after the 180° pulse (or after a period $\tau_d + t_v$ after the 90° pulse). When $\tau_d = \tau_s$, the first signal sample is taken which is associated with the predetermined image frequency pair $(-k_{xm}, -k_{ym})$, see FIG. 4b, and the signal samples taken during this measurement period $T_M$ will be associated with points (several of which are denoted by O) on a sawtooth line which covers the image frequency matrix $k_x$, $k_y$ if the following conditions are satisfied:

$$2 \cdot k_{xm} = \gamma \cdot \int_{T_M} G_{24} \cdot dt \text{ and } 2 \cdot k_{ym} = \gamma \cdot \int_{\frac{1}{2}t_y} G_{44} \cdot dt.$$

When a shorter preparation period $\tau'_D$ is chosen for a next measurement cycle, the alternating $G_y$ gradient field $G_{44}$ will already have exerted an effect on the excited nuclear spins for some time, so that the first signal sample taken at the starting instant of the measurement period $T_M$ will be associated with an image frequency pair $(-k_{xm}, k'_y)$ for which $-k_{ym} < k'_y \leq k_{ym}$ (see FIG. 4b). The signal samples to be taken thereafter are situated on a sawtooth line l' which passes through the point $(-k_{xm}, k'_y)$ and which has been shifted in the $k_x$-direction with respect to the sawtooth line 1. Several of these measurement points are denoted by x on the line l'. By performing several measurement cycles in succession while using each time a step-wise decreasing preparation period $\tau_D$, the $k_x - k_y$ image frequency plane can be filled with measurement points, so that after a signal transformation (2-D Fourier transformation in many cases) a 2-dimensional image of a nuclear magnetization distribution will be obtained. It is to be noted that the difference between the longest and the shortest preparation period $\tau_D$ need be at most $\frac{1}{2}t_y$ (the duration of the period of the periodic $G_y$ gradient field); in the example given in FIGS. 4a and 4b, the first signal samples taken are associated with image frequency pairs $(-k_{xm}, k_y)$ where $k_y$ extends from $-k_{ym}$ to $+k_{ym}$ and where the sawtooth line l, l', l'' (see FIG. 4b) always encloses the same (positive) angle with respect to the $k_y$-axis. By introducing a 180° phase reversal of the $G_y$ gradient field $G_{34}$ during the preparation period $(t_v + \tau_D)$ and also of the alternating, periodic $G_y$ gradient field $G_{44}$ to be subsequently generated, all other sawtooth lines which cover the image frequency pairs $(-k_{xm}, k_y)$, where $k_{ym} \geq k_y > -k_{ym}$, and which always enclose the same (negative) angle with respect to the $k_y$-axis can be followed. The $k_x - k_y$ plane will thus be uniformly filled with measurement points. The described method offers an important advantage in that all the signal samples associated with an image frequency $k_x$ have been taken at the same instant after the r.f. pulse $P_{24}$ ($P_{14}$); consequently:

$$k_x = \gamma \cdot \int_{t_v + \tau_s}^{t} G_{24} \cdot d\tau = \gamma \cdot G_{24} \cdot (t - t_v - \tau_s).$$

Because $t_v$ and $\tau_s$ are the same for each measurement cycle, $k_x = \gamma \cdot G_{24} \cdot t$—constant which can be selected and which can be made equal, for example to $k_{xm}$, so that, in effect, $k_x$ can be considered as representing "time". The advantage obtained by means of the described method consists in that the effect of field non-uniformities, of the relaxation time $T_2$ etc. on the signal samples associated with the same image frequency $k_x$ will always be the same, which results in a higher image quality (reduction of ghost images and blurring).

It will be apparent that it is possible to start a new measurement cycle with a 180° pulse after the measurement period $T_M$, followed by a preparation time $\tau'_D$ which is shorter than the preparation time $(t_v + \tau_D)$ during the preceding measurement cycle, the $G_x$ and $G_y$ preparation gradients $G'_{14}$ and $G'_{34}$, respectively, being applied during this preparation period $\tau'_D$. Furthermore, the half period of the alternating $G_y$ gradient field $G_{44}$ is divided, by way of example, into 11 sampling intervals $t_m$ (in reality there are 127, 255 or 511 intervals), so that a signal sample is taken for 12 different values of $k_y$, where $-k_{ym} \leq k_y \leq +k_{ym}$. It will be understood that for the described example a signal sample is taken twice for each measurement point $(k_x, k_y)$. Even though this results in an improved signal-to-noise ratio, more effective sampling diagrams (and associated adapted gradient fields) exist, as will be described hereinafter.

Figure 5B:
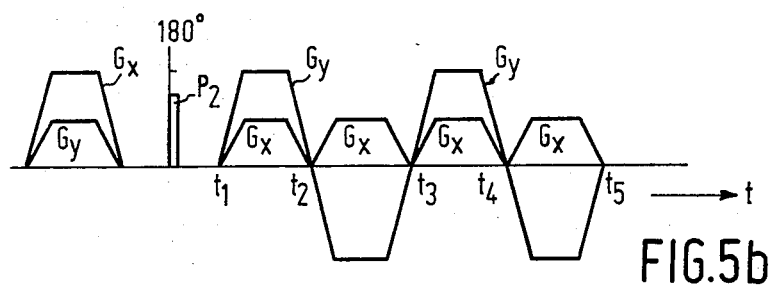
Figure 5C:
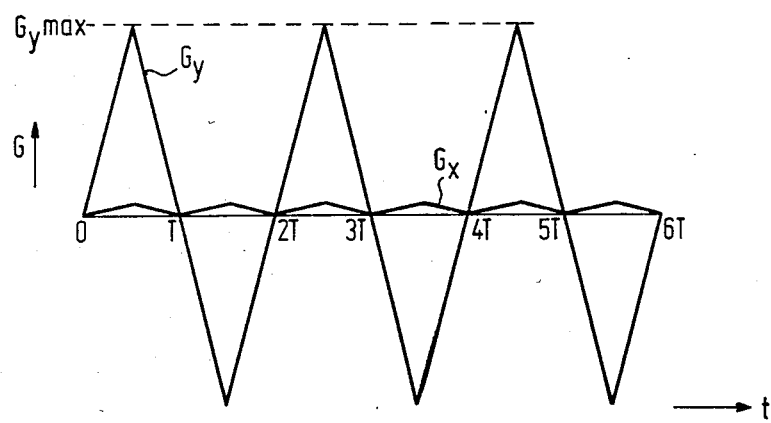

FIG. 5a shows examples of $G_x$ and $G_y$ gradient fields which are both periodic, with $G_y$ alternating as before, the amplitude of the $G_x$ gradient field each time amounting to a fraction (1/P) of the (absolute) value of the amplitude of the $G_y$ field. It is thus achieved, that, although the alternating $G_y$ gradient field varies sinusoidally as a function of time, the $k_x - k_y$ image frequency plane is always covered along straight lines in a regular sawtooth line pattern (see FIG. 3b). It will be apparent that this will also be the case for the trapezoid or delta amplitudes (with a constant ratio P) of the $G_x$ and $G_y$ gradient fields shown in the FIGS. 5b and 5c, respectively. The ratio P determines the number of line segments formed in the image frequency matrix by the sawtooth line pattern during a measurement period $T_M$. When P=10, 10 lines (rows) in the image frequency matrix are filled with measurement points as denoted by the line 1 in FIG. 3b. It will be apparent that the sawtooth lines in the successive measurement cycles must be shifted with respect to one another, for which purpose suitable $G_x$ and $G_y$ gradient fields are applied during a preparation period (for example, for the echo pulse $P_2$ in FIGS. 5a and 5b). The instants at which signal samples must be taken with these time-dependent gradient fields (so that the measurement points are situated at a constant, desired distance $\Delta k_y$ from one another, for example in the $k_y$-direction in the image frequency matrix) are already known from Netherlands Patent Application NL-A-82.03519.

For the selection/adjustment of a given measurement cycle with associated time intervals and (respective periodic and alternating) gradient field intensities, use is made of programmed computer means. In an embodiment of the device 15 (FIG. 2), the central control means 45 comprise a programmed computer 51 (VAX 11/730) including an input/output station 52 and an interface 53 (see FIG. 6), the outputs 55 thereof controlling the following sections of the device 15: the generators 19, 21 and 23 for the gradient field waveforms to be generated, the generator 25 for generating r.f. 90° excitation and r.f. 180° pulses, the receiver 27, the demodulator 28 and the sampling circuit 29 with the analog-to-digital converter 31. The outputs 55 are connected to said sections via the bus 50. The interface 53 actually comprises a number of parallel operating interfaces: a waveform generator for controlling the gradient field generators 19, 21, 23, an interface for controlling the r.f. generator 25, the receiver 27, the demodulator 28 etc.

A further version of a method in accordance with the invention will be described with reference to FIG. 7. According to the hereinbefore described methods, all image frequencies between $-k_{ym}$ and $+k_{ym}$ are covered by means of the periodic, alternating $G_y$ gradient field. According to the further version of the method to be described hereinafter, this approach is abandoned and only a part of the $k_y$ image frequency range is covered (for reasons yet to be explained) during a period of the alternating $G_y$ gradient field. For the following example it is assumed that an image comprising 512×512 pixels of a nuclear magnetization distribution is to be obtained. It is often desirable to have a "coarse" image (for example 64×64 pixels) of the nuclear magnetization distribution immediately available before the complete image is realized. Consequently, the image frequency matrix ($k_x$, $k_y$) shown in FIG. 7 is divided into three sections I, II, III; in section I there are situated those image frequency pairs ($k_x$, $k_y$) in the range $k_{-y32} \leq k_y \leq k_{y32}$; in section II are situated those image frequency pairs ($k_x$, $k_y$) in the range $k_{y33} \leq k_y \leq k_{y256}$; and in section III are situated those image frequency pairs ($k_x$, $k_y$) in the range $k_{-y33} \leq k_y \leq k_{-y256}$. During a first series of measurement cycles, all those signal samples are collected which are situated in said section I, for example using the methods described with reference to FIGS. 3a, b, or 4a, b. Because the amplitude for covering the section I in the $k_y$-direction in the present example amounts to only $\frac{1}{4}$ of the amplitude which would be required to cover all the $k_y$-values from $k_{-y256}$ to $+k_{y256}$, the frequency of the alternating gradient field $G_y$ may be four times higher, (i.e. the period may be one quarter the duration), so that the section I will have been completely filled with measurement points after a period of time which amounts to only $\frac{1}{4}$ of the period of time required to fill the entire $k_x$, $k_y$ image frequency matrix. Consequently, after one quarter of the entire measurement period for an image of 512×512 pixels an image comprising 64×64 pixels can be reconstructed by using the signal samples associated with the image frequency pairs ($k_x$, $k_y$) where $k_{-y32} \leq k_x \leq k_{x32}$ and $k_{-y32} \leq k_y \leq k_{y32}$. While the image comprising 64×64 pixels is being reconstructed (and thereafter), for example, first the section II and then the section III can be filled with sample points by means of the described methods, it merely being necessary to adapt the presetting by means of the $G_x$ and $G_y$ gradient fields during the preparation period, and also the amplitude (and if necessary the frequency) of the alternating $G_y$ gradient field.

When an image is to be reconstructed from the measurement data in the image frequency matrix ($k_x$, $k_y$) by means of Fourier transformation, the data must be situated on two systems of lines; for one system it must hold good that $k_x$=constant, and for the other system: $k_y$=constant. As is shown diagrammatically in FIG. 8, many of the measurement data points are not situated on a $k_x$-line but are in a slightly shifted position. If this shift $\Delta$ on a $k_y$-line (see line $k_{yn+1}$) is always the same, a 1-D Fourier transformation of the measurement data on the $k_y$-line can be performed, followed by a known linear phase correction. After that it is still necessary to perform the 1-D Fourier transformation (on the values on the lines $k_x$=constant) (the foregoing is also described in said Netherlands Patent Application NL-A-82.03519).

When the signal samples are taken using methods in which the $k_x-k_y$ frequency plane is covered along a regular sawtooth line, various possibilities exist for correcting said shift in the $k_x$-direction. For each line $k_y$=constant, two groups of signal samples can be distinguished: a first group which exhibits a shift $\Delta'$ to the left and a second group which exhibits a shift $\Delta$ to the right. Each of the two groups can be separately corrected by means of a Fourier transformation and a phase correction.

It has already been mentioned that during the regular (uniform) filling of the $k_x$, $k_y$ image frequency matrix while using an alternating, periodic gradient field, two signal samples are obtained for each image frequency pair ($k_x$, $k_y$) when a signal sample is taken in the successive measurement periods after each (constant) sampling interval. This double sampling results in an improved signal-to-noise ratio, but in fact the sampling rate is too high by a factor of two. One step could be to take only those signal samples associated with $2 \cdot n \cdot \Delta k_y$ with an increasing image frequency $k_y$ (see arrows 01 and 02 in FIG. 8), n being an integral member and $\Delta k_y$ the frequency difference between two neighbouring $k_y$-lines, and to take only those signal samples which are associated with $(2 \cdot n+1) \cdot \Delta k_y$ with a decreasing image frequency (see arrows n1, n2 in FIG. 8).

Figure 9B:
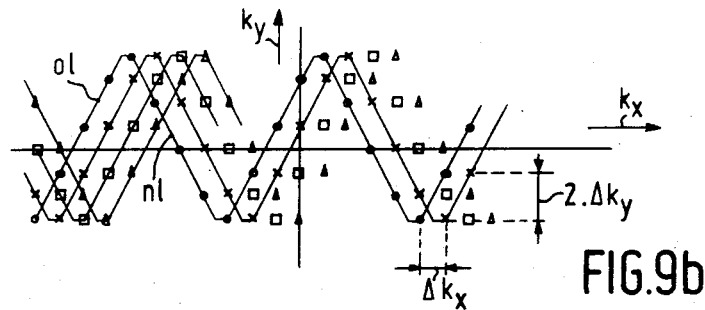

Another step would be to adapt the shape of the amplitude of the alternating gradient field. An example of such an amplitude is shown in FIG. 9a. Each half period of the alternating gradient field terminates with a "back-porch" with the amplitude equal to zero. The duration of this back-porch is preferably equal to half the sampling interval which may in this case be twice as long as the sampling interval used for a method as described with reference to FIGS. 3a, b and 4a, b. Half the duration of the period of the alternating gradient field preferably amounts to $(m+\frac{1}{2})$ or m times the duration of the long sampling interval, so that the maximum image frequency to be reached by means of the given amplitude shape is also reached and the signal samples of the negative-going line n1 are situated exactly halfway (as far as the image frequency $k_y$ is concerned) between the signal samples of the positive-going line o1 as shown in FIG. 9b. The proposed method results in a non-repetitive, uniform filling of the image frequency plane $k_x-k_y$.

Although the foregoing examples may have created the impression that the invention relates only to the determination of a nuclear spin density distribution, the invention can also be used advantageously for the determination of a $T_1$ relaxation time distribution, a $T_2$ relaxation time distribution, and a flow velocity distribution, and for location-dependent spectroscopy. In the latter case, for example no (constant) gradient field will be present during the measurement period (see FIGS. 3a and 4a) but only the image frequency $k_x$ will be "adjusted" during the preparation period. Furthermore, it is alternatively possible (for example, see FIGS. 3a and 4a) to shift the instant of the first sampling operation so that for a frequency pair ($k_x$, $k_y$) several tens of or more time-dependent signal samples are taken.

It is also to be noted that the description of spectroscopy measurements in accordance with the described methods can be used to determine nuclear spin density distributions in which image defects due to chemical shift ($\sigma$) and magnetic field non-uniformities which are caused by a non-ideal steady main field Bo (see FIGS. 1 and 2) and by local susceptibility differences, are (virtually) absent. The foregoing will be described in detail with reference to FIGS. 3a and b.

The measurement cycles for filling the entire $k_x$, $k_y$ matrix described with reference to FIGS. 3a and b are repeated a number of times (from 4 to 16 times), the starting instant of both gradient fields $G_x$ and $G_y$ for generating the echo pulse $P_2$ each time being different (the gradient field shapes $G_2$ and $G_4$ are both shifted with respect to the pulse P2). Instead of a two-dimensional matrix ($k_x$, $k_y$), a three-dimensional matrix ($k_x$, $k_y$, t) is now filled, a number (from 4 to 16) of time dependent measurement values then being available for each $k_x$-$k_y$ frequency pair. After signal transformation (a 3-D Fourier transformation), a three-dimensional matrix (x, y, ω) of values is obtained, so that for each pixel a (small) frequency spectrum (from 4 to 16 values) is determined. From the spectrum relating to each pixel, an intensity value can be selected relating to a given type of nucleus for the associated pixel (e.g. a proton chemically bound in fat or an unbound proton), so that a nuclear spin density distribution can be determined which is independent of the chemical shift. For the determination of a proton density distribution it is in principle only necessary to have available a frequency spectrum with only two intensity values (proton intensity for protons in water and for protons in fat). However, the non-uniformiities of the steady field cause a shift in the frequency of said two intensity values in the frequency spectrum (the position of or the frequency difference between the two values with respect to one another remains unchanged, because it is determined by σ in the spectrum). By determining a sufficiently wide frequency spectrum for each pixel, in which the frequency difference due to the chemical shift (σ) and the frequency shift caused by the non-uniformities is made "visible", a correct intensity value can be determined for the associated pixel in said spectrum by selecting the intensity value of the desired type of nuclear spin (i.e. that of protons in water or protons in fat).

It is also possible to carry out measurements without switching on the $G_x$ gradient magnetic field G2 during the measurement period $T_M$, so that the image frequency $k_x$ is adjusted during the preparation period. The samples taken during the measurement period $T_M$ will then be a function of $k_y$ and t (substituting t for $k_x$ in FIG. 3b) and will all be associated with the same value of $k_x$. Similarly, a 3-dimensional matrix ($k_x$, $k_y$, t) can also be filled with the described advantages.

What is claimed is:

1. A method of determining an NMR distribution in a region of a body which is situated in a steady, uniform magnetic field, said method including the steps of:
   (a) generating an r.f. electromagnetic pulse during a preparation period in order to cause a precessional motion of the magnetization of the nuclei in the body, thus generating a resonance signal,
   (b) then generating an alternating, periodic gradient magnetic field during a measurement period, said measurement period being divided into a plurality of sampling intervals during which a corresponding number of signal samples of the resonance signal are taken,
   (c) then repeating, each time after a waiting period, steps (a) and (b), the duration of the preparation period and/or the integral over the preparation period of at least one gradient magnetic field applied during the preparation period having a different value during each repetition in order to provide a set of signal samples from which, after a signal transformation thereof, an image of a nuclear magnetization distribution is determined, characterized in that the period of the sampling interval is at least a factor 2 shorter than the period of the alternating periodic gradient magnetic field which at most equals the measurement period.

2. A method of determining an NMR distribution in a region of a body which is situated in a steady, uniform magnetic field, said method including the steps of:
   (a) generating an r.f. electromagnetic pulse during a preparation period in order to cause a precessional motion of the magnetization of the nuclei in the body, thus generating a resonance signal,
   (b) then generating an alternating periodic magnetic field during a measurement period, said measurement period being divided in a plurality of sampling intervals during which a corresponding number of signal samples of the resonance signal are taken,
   (c) then repeating, each time after a waiting period, steps (a) and (b), the duration of the preparation period having a different value during each repetition in order to provide a set of signal samples from which, after a signal transformation thereof, an image of a nuclear magnetization distribution is determined, characterized in that the period of the sampling interval is at least a factor 2 shorter than the period of the alternating periodic gradient magnetic field which at most equals the measurement period, the starting instant of the alternating, periodic gradient magnetic field being coincident with the end of the preparation period, the measurement period commencing each time the same time interval after the r.f. electromagnetic pulse, so that at the starting instant of the measurement period, the phase of the alternating, periodic gradient magnetic field is always made different by using each time a different preparation period.

3. A method as claimed in claim 2, characterized in that a constant gradient magnetic field whose field direction extends perpendicularly to the field direction of the alternating, periodic gradient magnetic field is applied during the measurement period.

4. A method as claimed in claim 2, or 3, wherein said r.f. pulse generating step includes generating a 90° electromagnetic pulse and at least one 180° electromagnetic pulse for generating a nuclear spin echo signal defining said resonance signal from which samples are taken during a succeeding measurement period.

5. A method as claimed in claim 2, in which a further gradient field is applied during the measurement period, characterized in that the amplitude of the further gradient field amounts to a constant fraction of the amplitude of the alternating gradient field, the further gradient field always having the same field direction.

6. A method as claimed in claim 2, 3 or 5, characterized in that a preparation gradient magnetic field whose gradient direction is the same as that of the periodic, alternating gradient magnetic field is applied during the preparation period, the integral of the preparation gradient magnetic field over the duration of the preparation period having a different value during the successive preparation periods.

7. A method as claimed in claim 5, characterized in that a third gradient magnetic field whose field direction extends perpendicularly to the field directions of the alternating, periodic gradient magnetic field and the further gradient magnetic field is applied during the preparation period.

8. A method as claimed in claim 4, characterized in that during a measurement period, after every second 180° pulse, the direction of the periodic, alternating gradient field is reversed with respect to the alternating field during the measurement period prior to the second 180° pulse, the duration of the measurement period amounting to an integral number of periods of the alternating gradient magnetic field.

9. A method as claimed in claim 8, characterized in that each 90° pulse is followed by an even number of measurement periods.

10. A method as claimed in any one of claims 2, 3 or 5, characterized in that the periodic, alternating gradient magnetic field has zero intensity at the beginning or end of each half period for a period of time which is shorter than or equal to the sampling interval.

11. A method as claimed in any one of the claims 2, 3 or 5, characterized in that the intensity of the alternating gradient magnetic field is substantially proportional to its period.

12. A method as claimed in any one of the claims 2, 3 or 5, characterized in that during the measurement period only the alternating gradient field is applied so that, after the signal transformation of the signal samples, there is obtained for each pixel a frequency spectrum in which the intensities of nuclear spins, whether bound or not, can be distinguished, after which an image of a magnetization distribution of a given type of nuclear spin is formed by selecting for each pixel the intensity of a selected type of nuclear spin from the frequency spectrum associated with the relevant pixel.

13. A method as claimed in claim 2, characterized in that a constant gradient field is applied during the measurement period, the gradient directions of the constant gradient field being perpendicular to the gradient direction of the alternating gradient field and a gradient magnetic field is applied during the preparation period, the preparation period having a different value during each of said repetitions so that, after the signal transformation of the signal samples, a frequency spectrum is obtained for each pixel, in which the intensities of the nuclear spins, whether bound or not, can be distinguished, after which an image of a nuclear magnetization distribution of nuclear spins of the same type is formed by selecting the intensity of the selected type of nuclear spin for each pixel from the associated frequency spectrum.

14. A device for determining an NMR distribution in a region of a body, comprising:
 (a) means for generating a steady, uniform magnetic field,
 (b) means for generating r.f. electromagnetic radiation during a preparation period so as to produce processional motion of the magnetization of the nuclei in the body thereby generating a resonance signal,
 (c) means for generating a gradient magnetic field during said preparation period,
 (d) means for generating an alternating, periodic gradient magnetic field during a measurement period which follows said preparation period,
 (e) sampling means for taking signal samples of said resonance signal during said measurement period in the presence of said alternating gradient magnetic field generated by the means specified in paragraph (d),
 (f) processing means for processing the signal samples in order to obtain an NMR distribution, and
 (g) control means for controlling at least the means specified in paragraphs (b) to (f) so as to generate and sample a plurality of resonance signals during successive measurement cycles and process the signal samples taken during said measurement cycles, characterized in that the control means comprises programmed computer means for generating and applying control signals to the means for generating the alternating gradient magnetic field, said alternating gradient magnetic field having a period which is at least a factor 2 longer than the period of a sampling interval during which a given signal sample is taken and which at most equals the measurement period during which the resonance signal is sampled.

15. A device as claimed in claim 14, characterized in that the programmed computer means adjusts different preparation periods during successive measurement cycles, supplies a start pulse for the alternating gradient magnetic field so that the beginning thereof coincides with the end of the preparation period, and supplies a start pulse for the process of sampling the resonance signal, each time with the same time delay after the beginning of the preparation period.

16. A device as claimed in claim 14 or 15, characterized in that the means for generating the alternating gradient magnetic field generates an alternating periodic gradient field which has zero intensity at the beginning or end of each period for a period of time which is shorter than or equal to the sampling interval.

17. A device as claimed in claim 14, 15 or 16, characterized in that the processing means includes storage means for storing a frequency spectrum to be formed from the signal samples for each pixel of the image of the nuclear magnetization distribution to be determined and also includes selection means for selecting an intensity value for the associated pixel from each frequency spectrum.

18. A method as claimed in claim 1, wherein said r.f. pulse generating step includes generating a 90° electromagnetic pulse and at least one 180° electromagnetic pulse for generating a nuclear spin echo signal defining said resonance signal from which samples are taken during a succeeding measurement period.

19. A method as claimed in claim 1, in which a further gradient field is applied during the measurement period, characterized in that the amplitude of the further gradient field amounts to a constant fraction of the amplitude of the alternating gradient field, the further gradient field always having the same field direction.

20. A method as claimed in claim 1, 18 or 19, characterized in that a preparation gradient magnetic field whose gradient direction is the same as that of the periodic, alternating gradient magnetic field is applied during the preparation period, the integral of the preparation gradient magnetic field over the duration of the preparation period having a different value during the successive preparation periods.

21. A method as claimed in claim 19, characterized in that a third gradient magnetic field whose field direction extends perpendicularly to the field directions of the alternating, periodic gradient magnetic field and the further gradient magnetic field is applied during the preparation period.

22. A method as claimed in claim 18, characterized in that during a measurement period, after every second 180° pulse, the direction of the periodic, alternating gradient field is reversed with respect to the alternating field during the measurement period prior to the second 180° pulse, the duration of the measurement period amounting to an integral number of periods of the alternating gradient magnetic field.

23. A method as claimed in claim 22, characterized in that each 90° pulse is followed by an even number of measurement periods.

24. A method as claimed in claim 1, 18 or 19, characterized in that the periodic, alternating gradient magnetic field has zero intensity at the beginning or end of each half period for a period of time which is shorter than or equal to the sampling interval.

25. A method as claimed in claim 1, 18 or 19, characterized in that the intensity of the alternating gradient magnetic field is substantially proportional to its period.

26. A method as claimed in claim 1, 18 or 19, characterized in that during the measurement period only the alternating gradient field is applied so that, after the signal transformation of the signal samples, there is obtained for each pixel a frequency spectrum in which the intensities of nuclear spins, whether bound or not, can be distinguished, after which an image of a magnetization distribution of a given type of nuclear spin is formed by selecting for each pixel the intensity of a selected type of nuclear spin from the frequency spectrum associated with the relevant pixel.

27. A method as claimed in claim 1, characterized in that a constant gradient field is applied during the measurement period, the gradient directions of the constant gradient field being perpendicular to the gradient direction of the alternating gradient field and a gradient magnetic field is applied during the preparation period, the preparation period having a different value during each of said repetitions so that, after the signal transformation of the signal samples, a frequency spectrum is obtained for each pixel, in which the intensities of the nuclear spins, whether bound or not, can be distinguished, after which an image of a nuclear magnetization distribution of nuclear spins of the same type is formed by selecting the intensity of the selected type of nuclear spin for each pixel from the associated frequency spectrum.

* * * * *